United States Patent

Menes et al.

[11] Patent Number: 5,024,662
[45] Date of Patent: Jun. 18, 1991

[54] RESISTANCE SYRINGE FOR EPIDURAL ANESTHESIA

[76] Inventors: Cesar M. Menes, 12905 E. Wolverton, Cerritos, Calif. 90701; Cenon M. Menes, 212 N. County Line Rd., Hinsdale, Ill. 60521

[21] Appl. No.: 492,749
[22] Filed: Mar. 13, 1990
[51] Int. Cl.[5] .............................................. A61M 37/00
[52] U.S. Cl. .................................. 604/131; 604/218; 128/DIG. 12
[58] Field of Search ............... 604/131, 132, 133, 218, 604/187, 207, 208, 134, 135; 128/DIG. 12, DIG. 13

[56] References Cited

U.S. PATENT DOCUMENTS

| | | | |
|---|---|---|---|
| 4,381,006 | 4/1983 | Genese | 604/135 |
| 4,636,197 | 1/1987 | Chu | 604/207 X |

Primary Examiner—John D. Yasko
Attorney, Agent, or Firm—Natan Epstein

[57] ABSTRACT

An attachment for a loss of resistance syringe of the type used for inserting a epidural needle into the epidural space of a patient for administration of anesthesia includes an elastomeric band attached between diametrically opposed points of a ring dimensioned to slide onto the barrel and be retained against finger flange on the syringe, the band having a length such that an intermediate portion engaged to a thumb end of the syringe piston will bias the piston for return from a drawn to a depressed position for injecting the syringe contents, the band being characterized in that the bias is insufficient to inject the fluid into tissues normally encountered between the skin and the epidural space of a patient.

18 Claims, 1 Drawing Sheet

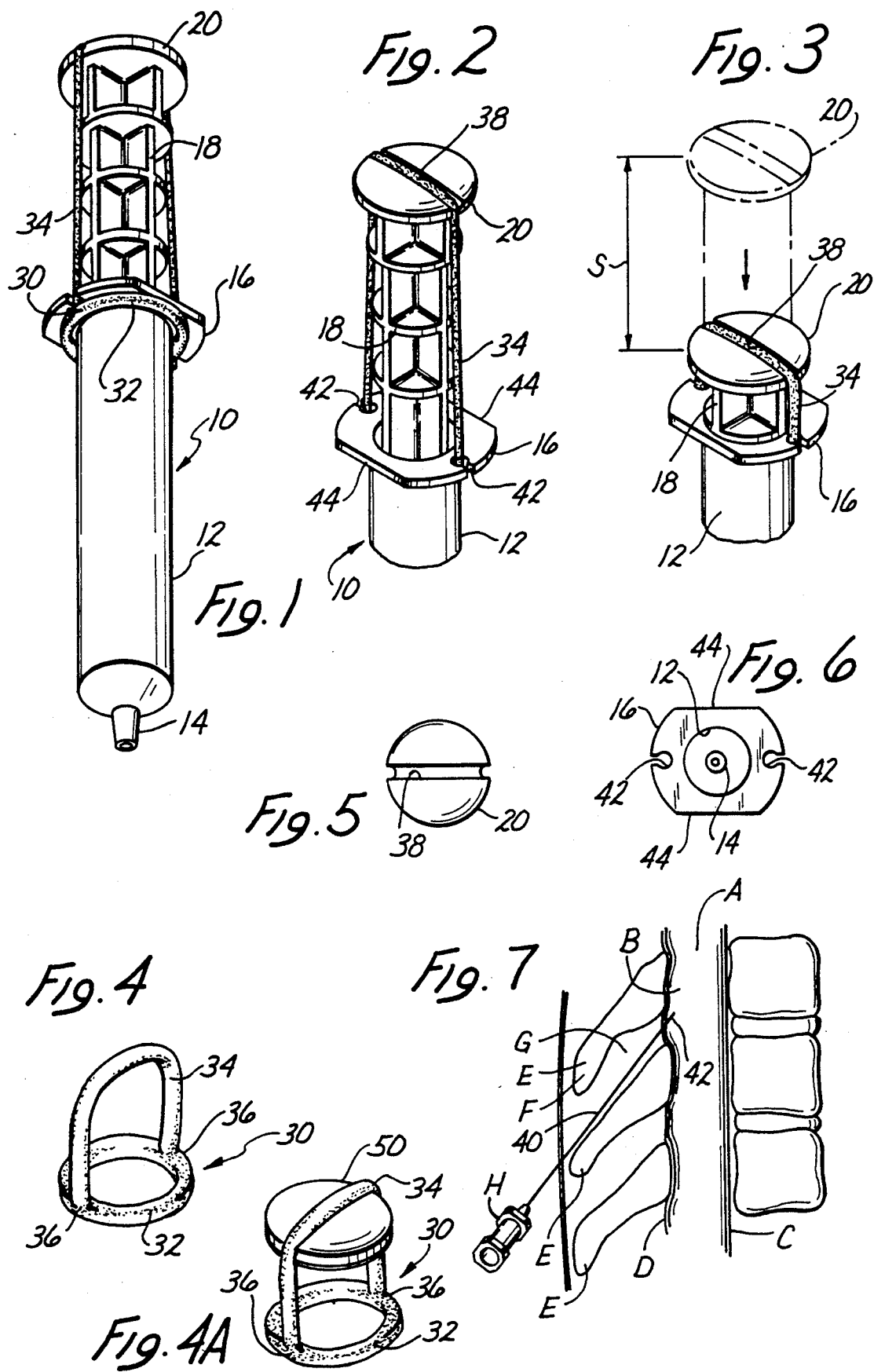

RESISTANCE SYRINGE FOR EPIDURAL ANESTHESIA

BACKGROUND OF THE INVENTION

Field of the Invention

The present invention pertains generally to the field of medical anesthesia and more particularly relates to improvements in resistance syringes used for accurately positioning an epidural needle in preparation for injection of anesthetic into the epidural space of the spinal cord.

Epidural anesthesia involves the injection of a suitable liquid anesthetic substance into the epidural space which surrounds the dura mater which in turn surrounds the spinal cord proper. The epidural space is defined between the ligamentum flavum on the posterior or back side of the spinal cord, and the anterior longitudinal ligament on the anterior or frontal side of the spinal cord. These flexible but tough ligaments interconnect the bony vertebrae which enclose and protect the spinal cord and spinal canal.

A dose of a suitable anesthetic such as lidocaine or bupivacaine, by way of example, produces a regional nerve block suitable for surgical procedures to be performed on portions of the anatomy affected by the nerve block, primarily but not limited to portions of the anatomy below the level of the spinal column at which the anesthetic is injected.

In the preferred midline technique the epidural needle passes through the supraspinous, interspinous and ligamentum flavum structures before entering the epidural space. Insertion of the needle into the epidural space is complicated by the lack of feedback as to the position of the needle tip, coupled with the imperative need to avoid puncturing the dura mater which surrounds the spinal cord, since there is potential for catastrophic trauma to the spinal cord with the epidural needle. Extreme caution must therefore be exercised in the positioning of the needle tip, which must pierce through the tough, resilient, leather-like ligamentum flavum and then stop immediately within the narrow epidural space, short of puncturing the dura mater.

The needle must be moved through the ligamentum flavum very slowly and in a carefully controlled fashion. At the same time, pressure is applied to the plunger of the attached syringe which is filled either with air or saline solution. The object is to continuously test for loss of resistance to injection, experienced when the needle lumen enters the epidural space after clearing the ligamentum flavum. This loss of resistance is experienced by little if any resistance to injected air or fluid, and a negative aspiration test then indicates that the needle lumen is properly positioned in the epidural space.

In order to appreciate the contribution being made by the present invention, it is important to understand the demands placed upon the anesthesiologist's dexterity by this procedure. It is of critical importance that the needle traverse the ligamentum flavum in a carefully measured and controlled manner. Typically, this is achieved by applying resistance to the advancing needle with the anesthesiologist's non-dominant hand (the left-hand if the anesthesiologist is right-handed) while the dominant hand applies pressure to the plunger to test for resistance to injection while at the same time slowly advances the needle. Variations of this technique may be adopted according to personal preference, for example the needle may be advanced continuously while pressure on the syringe barrel is also maintained continuously to test for resistance. In the alternative, the needle is advanced in very small increments, e.g. 1 millimeter, testing for resistance to injection after each advance.

The difficulty of correctly positioning the needle lumen in the epidural space has spurred many attempts to develop methods and devices for detecting and indicating correct needle placement. These expedients have generally exploited the low resistance to injection and subatmospheric pressure characteristic of the epidural space. One such technique involves placement of a drop of saline solution on the open hub of a epidural needle. The drop will be "sucked-in" as the needle lumen enters the epidural space where, for reasons not well understood, prevails sub-atmospheric pressure. Other means used for this purpose include capillary attachments with fluid indicators developed by Odom, or inflated balloons by MacIntosh, which deflate upon entering the epidural space. It is also known to use spring loading devices to facilitate the loss of resistance phenomena which occur as the epidural needle passes from the dense ligamentum flavum into the lesser resistance of the epidural space.

It is an object of this invention to provide a simple, reliable, inexpensive disposable attachment to a conventional syringe, in particular for use with syringes of the so-called resistance type which are specifically designed for low barrel friction to facilitate kinesthetic sensing of changes in resistance to injection as the epidural needle passes through various anatomical structures.

A continuing need exists for an aid which will ease the demands placed on the anesthesiologist's dexterity in performing this procedure without resort to esoteric mechanisms, unfamiliar devices which require special handling, are difficult to sterilize, and generally unnecessarily expand the already over-crowded medical armamentarium.

The device of this invention is an attachment to conventional syringes which are well-known and familiar to any anesthesiologist. The attachment is low cost, very simple in construction, reliable and easy to use with minimal or no training, and in no way impairs the sterile condition of the syringe when attached to the same. Further, given that the device is an attachment to conventional syringes already used for anesthesia procedures, the added expense is very small yet affording a substantial reduction in the difficulty of epidural anesthesia procedures, with a consequent increase in safety of the procedure.

Because of these qualities, the present invention is intended to overcome the difficulties and disadvantages associated with the many previous attempts to facilitate administration of administering this challenging form of anesthesia. Given the potential for irreparable, catastrophic injury if the needle is mishandled, any aid which will increase the confidence of the anesthesiologist in performing epidural injections is of great value.

SUMMARY OF THE INVENTION

This invention addresses the aforementioned difficulties by providing an attachment or accessory for a disposable syringe to facilitate guiding a epidural needle into the epidural space of a patient for administration of anesthesia. The invention contemplates both an integrated combination of a syringe fitted with the driver accessory, as well as a kit of parts consisting of the separate driver accessory for attachment to a syringe when needed.

The elastomeric driver accessory described below is for use with a syringe of the type including a syringe plunger slidable in a syringe barrel between a normal and a drawn position. The elastomeric driver has a band of elastomeric material retained to the syringe barrel at diametrically opposed points thereof, the band being stretchable over a thumb end of the plunger for biasing the plunger from the drawn position to the normal position. The elastomeric band is preferably attached to a retaining ring sized to slide onto the syringe barrel against the finger flange on the barrel.

The elastomeric element is characterized in that the bias applied to the syringe with the plunger in a drawn position is insufficient to inject a fluid contained in the barrel into living tissues normally encountered between the skin and the epidural space of a patient.

An intermediate portion of the elastomeric band is engaged in a retaining groove in the thumb rest of the plunger, or by other expedients such as adhesive, or a retaining cap fitted over the thumb rest and secured to the band.

BRIEF DESCRIPTION OF THE DRAWINGS

FIG. 1 is a perspective view of a syringe fitted with the spring loading attachment of this invention;

FIG. 2 is another perspective view of the syringe of FIG. 1 showing the elastomeric band fitted in a retaining groove in the thumb rest of the syringe;

FIG. 3 illustrates the displacement of the syringe plunger in response to the spring bias applied by the elastomeric band;

FIG. 4 is a perspective view of the elastomeric driver attachment of this invention for use with a pre-grooved syringe thumbrest as in FIG. 2;

FIG. 4A is a persepctive view of the elastomeric driver attachment of this invention for use with an ungrooved conventional syringe.

FIG. 5 is a top plan view of the thumb rest grooved for receiving the elastomeric element;

FIG. 6 is a top end view of the syringe barrel, the plunger being removed therefrom, showing the guide slots in the finger flange through which passes the elastomeric elements;

FIG. 7 is a sectional view taken medially along a thoracic portion of the spinal column showing a epidural needle inserted into the epidural space.

DETAILED DESCRIPTION OF THE PREFERRED EMBODIMENTS

FIG. 1 shows a syringe 10 which is of generally conventional construction in that it includes a barrel 12 with a tip 14 at a lower end and a finger flange 16 at its upper end. A plunger 18 terminates in a thumb rest 20 at its upper end and has a stopper (not shown) at its lower end interiorly to the barrel 12. The syringe 10 is made of molded plastic material and is a single use, disposable syringe. Such syringes are commercially available in many sizes and variations from numerous commercial suppliers. In particular, the syringe 10 may be of the type specifically constructed for loss of resistance testing and sold for example by Concord under the trademark Pulsator. Such syringes are characterized by relatively low frictional force between the stopper mounted on the plunger end and the interior surface of the syringe barrel.

FIG. 4 shows the accessory elastomeric driver 30 consisting of a retaining ring 32 which may be of any suitable relatively rigid material, and an elastomeric element 34 which in a currently preferred embodiment of the invention, is a length of latex rubber band secured at both ends to diametrically opposite points 36 of the ring 32.

The elastomeric driver is sized and configured to attach to the syringe 10 as shown in FIGS. 1-3. The inside diameter of the ring 32 is slightly oversized in relation to the exterior diameter of syringe barrel 12, so that ring 32 slides easily onto the barrel from the tip end 14 upwardly against the underside of finger flange 16.

Turn now to FIG. 7 which illustrates in medial section, the anatomy of the spinal column along a three vertebra segment in the thoracic region. The spinal cord encased in the dura mater A lies within the epidural space B bounded by the anterior longitudinal ligament C and the ligamentum flavum D. The spinal column segment illustrated includes three thoracic vertebrae E. A epidural needle 40 is shown between the laminae of adjacent vertebra, piercing the ligamentum flavum with the needle tip 42 lying within the epidural space.

Turning to FIG. 2 now, the syringe 10 is shown with the plunger 18 in drawn position against the spring loading of the elastomeric element 34. The elastomer 34 is attached to the retaining ring 32 which in FIG. 2 is hidden underneath the finger flange 16. The intermediate portion of the elastomer band 34 lies within a retaining groove 38 extending diametrically across the top surface of the thumb rest 20, as best seen in FIG. 5. The portions of the elastomeric band 34 which extend longitudinally on each side of the plunger 18 pass through guide slots 42 formed at diametrically opposite points of the finger flange 16, as best seen in the top end view of FIG. 6. The retaining groove 38 and guide slots 42 provided on the syringe 10 are not conventionally provided on commercially available syringes, and requires suitable modification to the injection molds used in the fabrication of such syringes. The addition of the guide slot and retaining groove just described do not in any significant manner impair conventional use of the syringe 10, i.e. without the elastomeric drive 30 of this invention, nor significantly add to the cost or difficulty of manufacture of the syringe.

The syringe 10 can be held single-handedly, with the dominant hand of the anesthesiologist, in the drawn position of FIGS. 1 and 2 while the needle 40 punctures the skin F. Once the needle lumen, at the tip 42, advances into the denser tissues, the anesthesiologist may release the hold on the plunger 18, maintaining hold only of the barrel 12 for better control while advancing and manipulating the needle 40 towards the epidural space. At this stage of the procedure, the needle lumen will be occluded by the ligamentous tissues intermediate the spinal laminae, effectively precluding injection of the air filling the syringe barrel 12 which is consequently maintained in a state of compression under the urging of the elastomer band 44. No longer must the anesthesiologist concentrate on testing for low resistance to injection at every fractional advance of the needle tip 42. As soon as the ligamentum flavum D is punctured by the needle tip and the needle lumen enters the epidural space, resistance to injection will be markedly reduced, allowing the plunger 18 to drive into the barrel 12 under the urging of the elastomer band 34, injecting a measure of air, or other fluid such as saline solution, into the epidural space. This event is immediately visually and otherwise apparent to the anesthesiologist who is then unambiguously informed of entry of the needle lumen in the epidural space. The low resistance to injection is a well-known property of the epidural space and is facilitated by a characteristic subatmospheric pressure in that space, a phenomenon the basis for which is not well understood.

Once the epidural needle 40 is correctly positioned for injection into the epidural space B, the syringe 10 may be detached from the needle hub H and a fresh syringe loaded with anesthetic is fitted to the needle hub H. The anesthetic may then be injected into the epidural space.

The immediate plunger movement upon penetration of the needle into the epidural space gives nearly instantaneous positional information to the anesthesiologist and is an improvement over the currently prevailing kinesthetic method of testing for low resistance, which relies upon the anesthesiologist being sufficiently skillful to continuously or very frequently test for resistance while at the same time advancing the needle towards the epidural space. The demands placed on the individual's skill are great in that he or she is required simultaneously to maintain proper needle orientation during the correct approach, a complex process in itself in the case of thoracic epidural puncture in that the paramedian approach requires the needle to puncture the skin initially along a line parallel to the spinal cord, and then make a series of corrections as the needle advances between the vertebra laminae by walking the needle along the laminae until it finds the ligamentum flavum at a steep angle. Requiring the anesthesiologist to maintain constant pressure on the syringe plunger while advancing the needle by feel along a difficult track substantially increases the difficulty as well as the risk of this procedure.

It is relatively easy for the needle tip to cross the narrow epidural space and inadvertently puncture the dura mater A, thereby potentially causing irreparable spinal damage. It is therefore highly beneficial to provide a means such as the driver 30 just described which will give the anesthesiologist immediate notice upon entry of the needle tip into the epidural space, thereby cautioning against further significant advance of the needle.

It is important to carefully select the elastomeric element 34 so as to provide the correct degree of spring loading to the plunger 18. The drive force should be sufficient to deliver unequivocal and easily observable plunger movement upon penetration of the epidural space. On the other hand, the loading force applied by the elastomer band 34 must be less than such force which would inject the contents of the syringe barrel against the greater resistance offered by the tissue layers G between the skin F and the ligamentum flavum D. If excessive loading forces are applied by the elastomer band 34, then the syringe contents will be injected even into relative dense ligamentous tissue, which would be most undesirable and misleading for purposes of this invention. FIG. 3 illustrates the stroke S of the syringe barrel traveled under the influence of the elastomeric band loading, from a drawn position suggested in phantom lining to a depressed or normal position shown in solid lining where the plunger 18 is driven into the syringe barrel 12, expelling the contents of the syringe barrel through the needle tip. It is desirable for the elastomer band 34 to maintain a small degree of tension or loading even in the depressed condition of the plunger so as to maintain engagement of the band within the retaining groove 38. After use, the elastomeric driver 30 may be discarded together with the syringe 10. It will be appreciated that sterilization of the syringe 10 does not necessarily require sterilization of the elastomeric driver 30. The driver accessory may be packaged separately from the syringe 10 in a clean but not necessarily sterile condition.

The retaining groove 38 and guide slots 42 are not essential to the ability to use the spring loading accessory with a conventional disposable syringe. It will be noticed that most disposable plastic syringes have a finger flange 16 shaped as shown, with a wide dimension, and a narrower dimension where the finger flanges do not greatly exceed the outer diameter of the barrel 12. If no guide slots 42 are provided on the finger flange, the retaining ring 32 may be rotated about the barrel 12 so as to position the longitudinal portions of the elastomer band 34 along the narrower portions 44 of the finger flange indicated at FIGS. 2 and 6.

Instead of a preformed retaining groove 38, other expedients may be adopted for securely engaging the intermediate portion of the elastomer band 34 to the thumb rest 20. Such expedients may include a cap 50 shown in FIG. 4A adapted to fit over and engage the thumb rest 20 of a conventional, unmodified syringe, this cap in turn being provided with a transverse retaining groove or other means engageable to or permanently secured to the elastomer band 34. In such an alternate construction of the elastomeric driver 30, the retaining ring 32 would be fitted over the syringe barrel 12, and the retaining cap would then be fitted over the thumb rest 20 of the syringe. The underside of the cap 50 may be provided with a layer of a suitable adhesive (labeled in FIG. 4A) normally protected by a cover sheet which can be peeled-off just prior to use. The cap 50 is then pressed to the thumb rest 20 of a conventional ungrooved, unmodified syringe 10 and is held securely in place by the adhesive while the anesthesia procedure is performed. The syringe along with the adhesively attached cap and driver 30 may be subsequently discarded.

While a preferred embodiment of the invention has been described and illustrated for purposes of example and clarity, it must be understood that many changes, substitutions and modifications to the described embodiments will become apparent to those possessed of ordinary skill in the art without thereby departing from the spirit and scope of the invention as set forth in the appended claims.

What is claimed is:

1. A disposable syringe for single handed use in guiding an epidural needle into the epidural space of a patient for administration of anesthesia, comprising:

a disposable syringe including a syringe plunger slidable in a syringe barrel between a normal position and a drawn position for discharging fluid contained in said barrel through said needle;

said barrel being attachable to the hub of an epidural needle;

a band of elastomeric material having two ends secured to said barrel at diametrically opposed points thereof;

said band having a portion intermediate said secured ends stretchable over a thumb end of said plunger for biasing said plunger from said drawn position to said normal position;

wherein discharge of fluid from said barrel through said needle is normally unrestricted thereby to unambiguously signal the penetration of the epidural space by said needle by immediate and easily perceptible plunger movement from said drawn to said normal position under bias of said band as a result of uncontrolled injection of said fluid into the epidural space.

2. The syringe of claim 1 further comprising means for securing an intermediate portion of said band to said thumb end.

3. The syringe of claim 1 wherein said band is secured to a ring slidably fitted onto said barrel against finger flange means provided at one end of said barrel.

4. A disposable syringe for use in inserting an epidural needle into the epidural space of a patient for administration of anesthesia, comprising:
   a disposable syringe including a syringe plunger slidable in a syringe barrel between a normal and a drawn position for discharging fluid contained in said barrel through said needle;
   said barrel having finger flange means at one and and an opposite end attachable to the hub of an epidural needle;
   a band of elastomeric material retained to said barrel adjacent said finger flange means and engageable with a thumb end of said plunger for biasing said plunger from said drawn to said normal position such that said barrel is unrestricted by said band along a major portion of its length between said flange means and said opposite end so that the barrel may be manipulated for guiding said needle through the patient's tissues without interference with said bias;
   such that the holder of the syringe is alerted to penetration of the epidural space by plunger movement toward said normal position as a result of injection of said fluid into the epidural space under bias of said band.

5. A disposable attachment for a syringe of the type used for inserting an epidural needle into the epidural space of a patient for administration of anesthesia, the syringe having a barrel with finger flange means at one end and an opposite end attachable to the epidural needle, and a plunger movable in said barrel responsive to force applied to a thumb end thereof, said attachment comprising:
   a band of elastomeric material having two ends secured to a ring dimensioned to fit onto the barrel of the syringe against said finger flange means, said band having a length such that an intermediate portion engaged to a thumb end of the syringe plunger will bias the plunger for return from a drawn to a normal position for ejecting fluid in the syringe barrel without obstructing manual grasp of said barrel for guidance of said needle toward the epidural space through intervening tissues.

6. The attachment of claim 5 further comprising means for securing an intermediate portion of said band to a thumb end of the syringe plunger.

7. A kit of parts for use in the administration of epidural anesthesia, comprising:
   a disposable syringe including a syringe plunger slidable in a syringe barrel between a drawn and a normal position for discharging the contents of said barrel through said epidural needle;
   an epidural needle having a hub attachable to said barrel; and
   an elastomeric driver comprising a ring dimensioned to be retained against finger flange means on said barrel, and a band of elastomeric material secured to said ring and to a thumb end of the syringe plunger for biasing the plunger from a drawn to a normal position for ejecting fluid in the syringe barrel;
   such that said plunger will remain in said drawn position against said bias so long as said needle traverses tissue overlying the epidural space and will eject the contents of said barrel only upon entering the epidural space, fluid discharge from said barrel through said needle being normally unrestricted to thereby signal proper positioning of said needle in the epidural space by immediate and unambigous movement of said plunger into said barrel.

8. The attachment of claim 6 wherein said means for securing comprise means for adhesively securing said badn to said thumb end.

9. The attachment of claim 6 wherein said means for securing comprise a cap element attachable to said thumb end and means for engaging said intermediate portion to said cap.

10. The attachment of claim 9 wherein said cap element comprises adhesive means for securing said cap element to said thumb end.

11. A disposable attachment for a syringe of the type used for inserting an epidural needle into the epidural space of a patient for administration of anesthesia, the syringe having a barrel with finger flange means at one end and an opposite end attachable to the epidural needle, and a plunger displaceable within said barrel under force applied to a thumb end of said plunger, said attachment comprising:
   a band of elastomeric material having two ends retained to diametrically opposed points of an element dimensioned to fit onto the barrel of the syringe and be retained against said finger flange means, a cap element having adhesive means for securing said cap element to said thumb end of the plunger, and means securing an intermediate portion of said band to said cap element, so as to bias the plunger for return from a drawn to a normal position for ejecting fluid in the syringe barrel without obstructing manual grasp of said barrel for guidance of said needle toward the epidural space through intervening tissues.

12. A kit of parts for use in the administration of epidural anesthesia, comprising:
   a disposable syringe including a syringe plunger slidable in a syringe barrel between a drawn and a normal position for discharging the contents of said barrel through said epidural needle;
   an epidural needle having a hub attachable to said barrel; and
   an elastomeric driver comprising a ring dimensioned to slidably fit onto the barrel of the syringe and be retained against finger flange means on the syringe, and a band of elastomeric material having two ends retained to diametrically opposed points of said ring, said band having a length such that an intermediate portion engaged to a thumb end of the syringe plunger will bias the plunger for return from a drawn to a normal position for ejecting fluid in the syringe barrel such that grasp of said barrel is unrestricted by said band along a major portion of its length between said flange means and said opposite end so that the barrel may be manipulated for guiding said needle through the patient's tissues without interference with said bias;

such that said plunger will remain in said drawn position against said bias while the needle lumen is occluded by tissue overlying the epidural space and will eject the contents of said barrel only upon entering the epidural space thereby signaling proper positioning of said needle in the epidural space by movement of said plunger into said barrel.

13. The syringe of claim 4 wherein said band is secured to a ring slidably fitted onto said barrel against finger flange means provided at one end of said barrel.

14. A method for ascertaining entry of an epidural needle into the epidural space of a patient, comprising the steps of:

providing a disposable syringe including a syringe plunger slidable in a syringe barrel between a drawn and a normal position for discharging the contents of said barrel through said epidural needle;

attaching the hub of an epidural needle to said barrel;

securing an elastomeric element to said syringe barrel and to the thumb end of the syringe plunger so as to bias the plunger for return from a drawn to a normal position for ejecting fluid in the syringe barrel;

drawing said plunger to said drawn position to admit fluid into said barrel:

inserting the lumen of said needle into the patient's tissues overlying the epidureal space while holding said plunger in said drawn position against the bias of said elastomeric element; and releasing said plunger; manipulating the barrel for guiding said needle lumen into the epidural space;

so that said plunger is held in said drawn position against continuous bias by said elastomeric element so long as the needle lumen traverses tissue overlying the epidural space and will eject the contents of said barrel only upon entering the epidural space thereby signaling proper positioning of said needle lumen in the epidural space by movement of said plunger into said barrel.

15. The method of claim 14 wherein said elastomeric element is secured without obstructing a major portion of the barrel length between said flange means and said opposite end so that the barrel may be manipulated without interference with said bias.

16. The method of claim 14 wherein said step of securing comprises the steps of:

providing an elastomeric element secured to ring means slidable onto said syringe barrel against said finger flange;

sliding said ring means onto said syringe barrel against said finger flange means;

and engaging said elastomeric means with said thumb end of said plunger such that the elastomeric element is stretched between said ring means and said thumb end.

17. The method of claim 15 wherein said fluid drawn into said barrel is air.

18. A method for ascertaining entry of an epidural needle into the epidural space of a patient, comprising the steps of:

providing a syringe including a syringe plunger slidable in a syringe barrel between a drawn and a normal position for discharging the contents of said barrel through said epidural needle;

attaching the hub of an epidural needle to said barrel;

securing an elastomeric element to said syringe barrel and to the thumb end of the syringe plunger so as to bias the plunger for return from a drawn to a normal position for ejecting fluid in the syringe barrel;

drawing said plunger to said drawn position to admit air into said barrel:

inserting the lumen of said needle into the patient's tissues overlying the epidureal space while holding said plunger in said drawn position against the bias of said elastomeric element;

releasing said plunger; and manipulating the barrel for guiding said needle lumen into the epidural space;

so that said plunger is held in said drawn position against continuous bias by said elastomeric element so long as the needle lumen is occluded by tissue overlying the epidural space and will inject the air in said barrel upon entering the epidural space thereby unambiguously signaling proper positioning of said needle lumen in the epidural space by immediately perceptible movement of said plunger into said barrel.

* * * * *